(12) United States Patent
Gross et al.

(10) Patent No.: US 9,262,444 B2
(45) Date of Patent: Feb. 16, 2016

(54) SYSTEMS AND METHODS FOR APPLYING SERIES LEVEL OPERATIONS AND COMPARING IMAGES USING A THUMBNAIL NAVIGATOR

(75) Inventors: Ryan Wayne Gross, Barrington, IL (US); Joseph Carroll, Barrington, IL (US); Donnna Klem, Barrington, IL (US); Christopher Yunker, Barrington, IL (US); Naveed Rabbani, Hoffman Estates, IL (US); Benjamin Novatzky, Oak Park, IL (US)

(73) Assignee: General Electric Company, Schenectady, NY (US)

( * ) Notice: Subject to any disclaimer, the term of this patent is extended or adjusted under 35 U.S.C. 154(b) by 536 days.

(21) Appl. No.: 12/954,282

(22) Filed: Nov. 24, 2010

(65) Prior Publication Data

US 2012/0131498 A1    May 24, 2012

(51) Int. Cl.
*G06F 3/0484* (2013.01)
*G06F 17/30* (2006.01)
*G06F 19/00* (2011.01)

(52) U.S. Cl.
CPC ........ *G06F 17/30274* (2013.01); *G06F 19/321* (2013.01)

(58) Field of Classification Search
CPC ............ G06F 17/30247; G06F 3/0484; G06F 17/30274; G06F 19/321; G06T 11/00; G06T 7/0012
USPC ......................................................... 715/788
See application file for complete search history.

(56) References Cited

U.S. PATENT DOCUMENTS

| | | | |
|---|---|---|---|
| 5,801,700 A | 9/1998 | Ferguson | |
| 5,954,650 A * | 9/1999 | Saito et al. | 600/425 |

(Continued)

FOREIGN PATENT DOCUMENTS

| | | |
|---|---|---|
| CN | 100447786 C | 12/2008 |
| CN | 101398742 A | 4/2009 |

(Continued)

OTHER PUBLICATIONS

Fujifilm Medical Systems, Synapse Product Data, Synapse Release Version 3.2.1, Workstation Software, http://www.fujimed.com/products-services/network-systems/synapse/doc/workstation.pdf, retrieved online Sep. 23, 2011. (4 pages).

(Continued)

*Primary Examiner* — Alvin Tan
(74) *Attorney, Agent, or Firm* — Hanley, Flight and Zimmerman, LLC

(57) ABSTRACT

An example image layout and display navigator system includes a navigator that includes a miniature layout representation corresponding to the layout of images on the display. The navigator is to appear on the display based on user action with respect to displayed content and to allow a user to select an image series via the miniature layout and to select one or more series level operations for application to the image series via the miniature layout. The navigator is to apply a selected series level operation to the image series via the miniature layout based on user input. An action in one of the navigator and the display is to translate into a corresponding action on the other of the navigator and the display. The content display manager is to update the content displayed to reflect the selected series level operation applied to the image series.

21 Claims, 8 Drawing Sheets

(56) References Cited

U.S. PATENT DOCUMENTS

| | | | |
|---|---|---|---|
| 5,987,345 A * | 11/1999 | Engelmann et al. | 600/407 |
| 6,664,972 B2 * | 12/2003 | Eichel et al. | 345/582 |
| 6,734,880 B2 | 5/2004 | Chang et al. | |
| 7,058,901 B1 | 6/2006 | Hafey et al. | |
| 7,213,051 B2 * | 5/2007 | Zhu et al. | 709/205 |
| 7,337,403 B2 * | 2/2008 | Pavley et al. | 715/747 |
| 7,349,859 B1 | 3/2008 | Lamer et al. | |
| 7,634,733 B2 | 12/2009 | Sadikali et al. | |
| 8,225,199 B2 | 7/2012 | Okubo et al. | |
| 8,397,170 B2 * | 3/2013 | Araoka | 715/764 |
| 2003/0038846 A1 * | 2/2003 | Hori et al. | 345/809 |
| 2003/0137545 A1 * | 7/2003 | Hoehn | G06F 17/212 715/838 |
| 2003/0174872 A1 * | 9/2003 | Chalana | G06K 9/00 382/128 |
| 2004/0068423 A1 | 4/2004 | Shaw | |
| 2006/0085407 A1 | 4/2006 | Kaminaga et al. | |
| 2006/0238546 A1 * | 10/2006 | Handley | H04N 1/0035 345/619 |
| 2007/0063998 A1 | 3/2007 | Mahesh | |
| 2007/0064984 A1 | 3/2007 | Vassa et al. | |
| 2007/0101291 A1 | 5/2007 | Forstall et al. | |
| 2007/0127790 A1 | 6/2007 | Lau et al. | |
| 2007/0242069 A1 | 10/2007 | Matsue et al. | |
| 2008/0163070 A1 | 7/2008 | Mahesh et al. | |
| 2010/0131890 A1 | 5/2010 | Natanzon et al. | |
| 2011/0004839 A1 * | 1/2011 | Cha et al. | 715/765 |
| 2011/0222753 A1 * | 9/2011 | Kotula et al. | 382/132 |
| 2013/0058549 A1 * | 3/2013 | Djeridane | 382/128 |

FOREIGN PATENT DOCUMENTS

| | | |
|---|---|---|
| CN | 101527135 A | 9/2009 |
| JP | 2010187758 A | 9/2010 |

OTHER PUBLICATIONS

Anonymous, "Sending: Drag and Drop Onto a Contact Name," Sharing Files Yahoo, Retrieved from Internet: URL: http://help.yahoo.com/tutorials/ms8m/mess/im_file4.html, Retrieved Jul. 13, 2010. (2 pages).

International Search Report and Written Opinion issued in connection with PCT/US2009/065262, Sep. 27, 2010.

Unofficial English translation of Chinese Office Action issued in connection with corresponding CN Application No. 201110393144.4 on Jul. 29, 2015.

* cited by examiner

SYSTEMS AND METHODS FOR APPLYING SERIES LEVEL OPERATIONS AND COMPARING IMAGES USING A THUMBNAIL NAVIGATOR

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam" typically includes one or more series of images, such as images exposed before and after injection of contrast material or images with different orientation or differing by any other relevant circumstance(s) of imaging procedure. The digital images are forwarded to specialized archives equipped with proper means for safe storage, search, access, and distribution of the images and collateral information for successful diagnostic interpretation.

BRIEF SUMMARY

Certain examples provide systems, methods, and apparatus for image layout and display on a display such as a PACS workstation display.

Certain examples provide a computer-implemented method for image review and series operations using a navigator for a display. The method includes displaying a navigator interface in conjunction with a layout of images on a display. The navigator provides a miniature layout representation corresponding to the layout of images on the display. The method includes accepting user selection of an image series via the navigator miniature layout. The method includes providing one or more series level operations for application to the image series via the miniature layout. The method includes applying a selected series level operation to the image series via the miniature layout based on user input. The method includes updating display of the layout of image on the display based on the selected series level operation.

Certain examples provide an image layout and display navigator system. The system includes a content display manager to control content displayed for a user on a display. The content is to be organized on the display according to a display layout including multiple regions. The system includes a navigator to include a miniature layout representation corresponding to the layout of images on the display. The navigator is to appear on the display based on user action with respect to displayed content and to allow a user to select an image series via the miniature layout and to select one or more series level operations for application to the image series via the miniature layout. The navigator is to apply a selected series level operation to the image series via the miniature layout based on user input. An action in one of the navigator and the display is to translate into a corresponding action on the other of the navigator and the display. The content display manager is to update the content displayed to reflect the selected series level operation applied to the image series.

Certain examples provide a tangible computer readable medium having a set of instructions for execution on a processing device, the set of instructions implementing image layout and display navigator system. The system includes a content display manager to control content displayed for a user on a display. The content is to be organized on the display according to a display layout including multiple regions. The system includes a navigator to include a miniature layout representation corresponding to the layout of images on the display. The navigator is to appear on the display based on user action with respect to displayed content and to allow a user to select an image series via the miniature layout and to select one or more series level operations for application to the image series via the miniature layout. The navigator is to apply a selected series level operation to the image series via the miniature layout based on user input. The content display manager is to update the content displayed to reflect the selected series level operation applied to the image series.

Certain examples provide a computer-implemented method for image preview and layout using a navigator. The method includes displaying a navigator interface in conjunction with a layout of images on a display, the navigator providing a miniature layout representation corresponding to the layout of images on the display. The method includes accepting user selection, via the navigator miniature layout, of an image series that is not currently displayed. The method includes providing a preview of a layout of the selected image series to the user via the miniature layout. The method includes updating the display, upon user approval, based on the selected image series layout.

Figure 1:
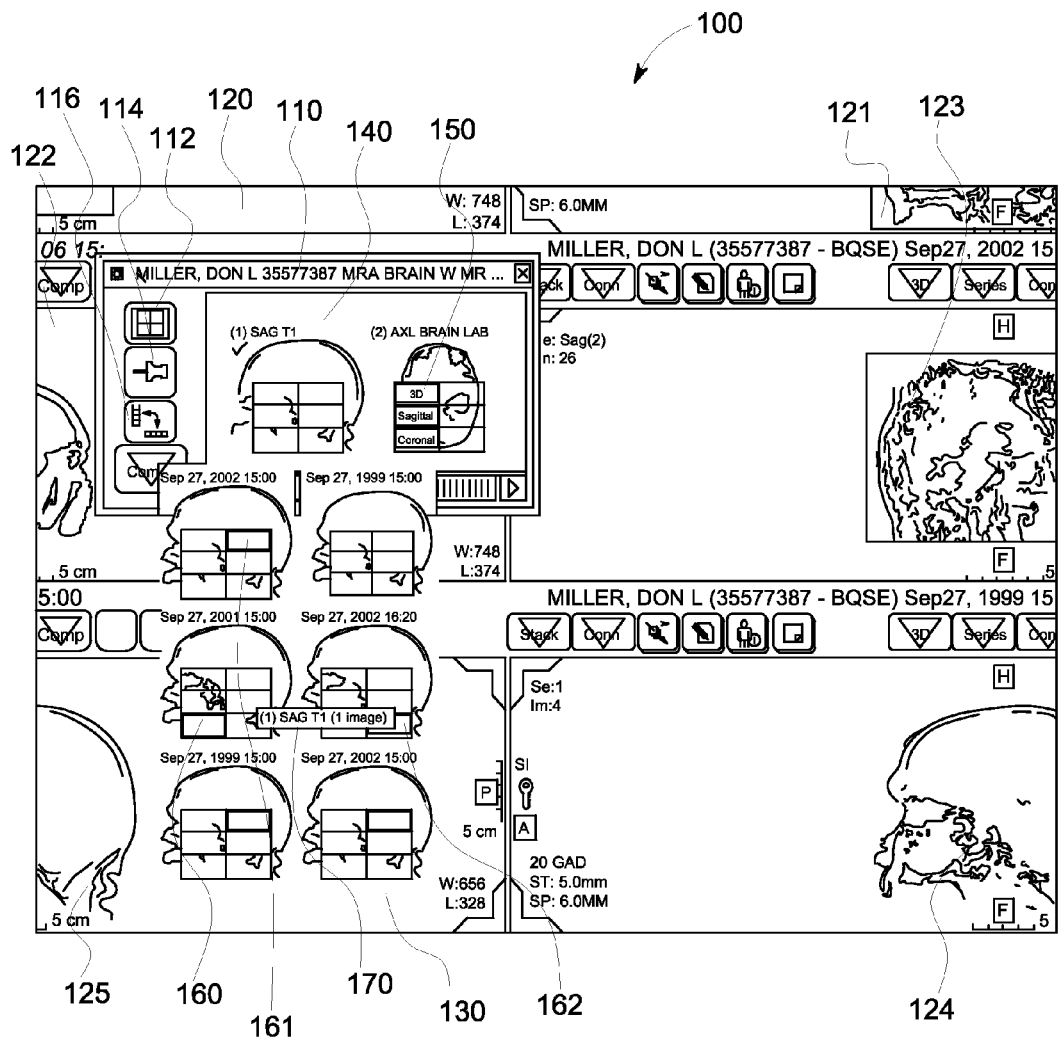
FIG. 1 depicts an example user interface for reviewing images.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, Blu-ray, etc., storing the software and/or firmware.

Certain examples provide a representation of one or more image groupings including one or more exams in the history of one or more patients.

Certain examples provide systems and methods to represent a layout of one or more image display areas spread across one or more monitors. For example, a layout representation can be displayed in close proximity to or on the image group representation(s). A layout representation can display a current allocation of the image groups to the image display areas (e.g., mini-layout), for example.

Certain examples provide systems and methods to specify an application of one image group to an image display region (e.g., by dragging it to a region or mini-region).

Certain examples provide systems and methods to apply series level operation(s) to the images as the operation(s) are applied to the region. For example, series level operations can be represented for application via the mini-layout. Condition(s) that preclude application of a series level operation can be provided when the user requests it/them, for example.

In certain examples, a navigator window includes one or more groups of images (e.g., series) each represented by a thumbnail. The thumbnail(s) match what is currently loaded in each image region, for example. A user can drag and drop a thumbnail onto one or more monitor regions to load a desired series. A user can drag and drop from the thumbnail to an image region to apply that image group to the region, for example.

In certain examples, a navigator tool can be launched in conjunction with one or more hanging protocols. For example, the navigator can be used preview a new image series allocation to be applied by a hanging protocol.

In certain examples, a monitor layout is displayed on a thumbnail, which supports drag and drop onto the layout on the same thumbnail. In certain examples, a mode is provided in which current image region allocation can be displayed by displaying monitor layouts on thumbnails with currently loaded series. In certain examples, rendering of images in the navigator reflects what has been applied in the image region. In certain examples, a monitor layout can be displayed in conjunction with other exam-specific information.

In certain examples, series level operations can be applied to an image group while the image is dragged to a region (or mini-region). Series level operations can be triggered by an action such as a key press, voice command, secondary mouse button, etc. The user can be visually notified of the operation(s) to be applied as the user is dragging the image, for example. For example, a description can be provided and/or a preview thumbnail of the modified image can be shown.

In certain examples, current operation(s) applied to an image group can be represented on a navigator mini-layout.

In certain examples, a user can be warned about conditions that may/will affect his/her series level operation(s).

A variety of operations can be applied to one or more images and/or groups of images via the mini-layout navigator. For example, three-dimensional (3D) reformatting of an image series (e.g., multiplanar reformation (MPR), volume rendering, 3D maximum intensity projection (MIP), etc.). Operations can be applied to some or all images in a selected series. For example, filters, window width and/or level, zoom/pan, de-bone, etc., can be applied to some or all images in the series. In certain examples, interactions between two or more series can be examined (e.g., PT/CT fusion, image subtraction, etc.).

In certain examples, a monitor layout can be changed while an image is dragged to a region. The layout change can be triggered by an action such as a key press, voice command, secondary mouse button, etc. The user can be visually notified of the operation(s) to be applied as the user is dragging the image, for example. For example, the mini-layout can be re-drawn to show the new monitor layout that will be applied.

In certain examples, special image groups (e.g., significant images, all images group, key image notes, etc.) are supported. In certain examples, predefined layouts are provided for special functionality (e.g., standard MIP/MPR views, mammography views, significant image views, etc.). In certain examples, an image up-count changes based on an applicable modality and/or procedure type.

In certain examples, a variety of features can be provided via a navigator tool and associated layout. For example, comparison previewing, multi-image preview sheets, intelligent repositioning, artificial intelligence, positioning of non-image data, etc., can be provided. For example, comparison previewing offers a quick and intuitive way of hanging desired comparison exam series. When a thumbnail is dragged over a region, a multi-image preview sheet of the series can intuitively be built and shown, for example. With intelligent repositioning, a navigator tool intelligently identifies and locates itself on a display wherever the navigator would least obstruct image anatomy or diagnosis information, for example.

In certain examples, artificial intelligence can be applied to change monitor layouts. For example, when a thumbnail is dropped onto the monitor region, the navigator uses built-in intelligence to determine and change an image up count of a region that would most suit the modality, procedure and/or body-part to be displayed.

In certain examples, non-image data can be positioned and displayed in one or more regions of a display. For example, the navigator allows the user to drop web services over a monitor region; to launch third-party applications such as Microsoft Word™; access clinical reports; and/or position any other non-image data or application on a region.

In certain examples, a navigator tool is launched with an exam context for the exam being displayed. The navigator displays the exam series and other related medical objects as image thumbnails. Dragging and dropping a thumbnail into a display region via the navigator loads the corresponding series in the display region in which the thumbnail was dropped. A set of tools is provided to change between comparisons, display a miniature representation of a monitor layout, etc.

Certain examples include a preview navigator for exam comparison. While a radiologist is viewing an exam, he/she often wants or needs to search for a comparison series. To do this, the radiologist can utilize a list of patient exams, a timeline view of the patient's exams, and/or a list of series for a given procedure body part, for example. However, these views provide only a textual or icon representation of the series, and do not show the user what the series will look like. With the preview navigator, whenever the user interacts with an exam (for example, by hovering a cursor over an image), a navigator is shown to navigate and drag/drop one or more series from the exam onto the current display. The user is able to quickly load the desired series and without experimental image loading, for example.

In certain examples, comparison exams are provided as a pop-out from the navigator. When a radiologist is looking for a comparison series for an exam he/she is currently reading, the series that he/she is most likely to be looking for is similar to the series in the current exam. The navigator can enable a user to select a series from the current exam (for example, by clicking a thumbnail representation in the navigator), and then uses an algorithm to match the current series to those in potential comparison exams. Following the matching, thumbnail representation(s) of matched series are popped out or displayed near the original series being reviewed, for example. These thumbnails can then be displayed along with thumbnails from the original exam.

A limitation of current image navigators is that each series is represented by a single thumbnail image, which, for scans involving multiple body parts, may not represent all of the data that is in the series appropriately. With the advent of fast computed tomography (CT) scanners leading to an increase in full body scans, this deficiency is becoming more pronounced. In an example multi-image preview mode, the navigator allows a series to be previewed over a number of images rather than a single image. For example, in order to select the images for previewing, the navigator tool intuitively captures relevant images such as key and significant images, and looks for images containing recent region(s) of interest (ROI), annotations, etc. These preview images are then shown to the user. In an example, when the user drags a thumbnail over a monitor region, associated preview images are displayed to the user in a sheet mode. In another example, the preview images can be shown as a pop-out near the original thumbnail image. The user can then choose to release the mouse/key to load the series, if desired.

Another limitation of current image navigators is the screen real-estate that they occupy. Either they appear above the image viewing regions, in which case they obscure image data, or they appear beside them, in which case they shrink the space available for reading images. Certain examples provide intelligent repositioning, which utilizes region information (e.g., title bars, locations, etc.) and/or pixel information (e.g., non-anatomy location) to determine a location for navigator launch that does not conceal image information. Additionally, the user can "pin" or position the navigator at a location for a certain modality, procedure, monitor layout, etc. The location can then be stored independently of the monitor resolution, for example.

Radiologists can review data pertaining to the current case that includes non-image data (e.g., reports, notes, radiology information system (RIS) data, and/or other special third-party application, etc.). Typically, to review non-image data, a system external to a picture archiving and communication system (PACS) is opened to retrieve and view the non-image information. In certain examples, an algorithm can be used to match data in relevant external system(s) to the current exam. The navigator system then obtains the data (e.g., from web services) and generates a preview of the information (e.g., a thumbnail). The preview (e.g., the thumbnail) is then displayed alongside the image series thumbnails, and the user can drag the preview to an image region to display a full-sized representation of the data in the layout, for example.

A metric used by modern radiology departments is an efficiency at which radiologists can read their exams. However, due to new, complicated operations that can be performed to provide better diagnostic results, more time is spent setting up the exam before it can be read. Thus, any time spent hanging the series that will be read is viewed as wasted time. In current radiology systems, the process of selecting a correct image series to hang can be long and tedious, often requiring the user to open several series while searching for the correct series. This process is further exacerbated when the user must review non-image data, such as a report or patient chart, which often involve opening a completely different system. This creates a conflict of interest for the radiology departments, which must trade-off between the rate at which they can read exams and the level of diagnostic support they obtain from the software they utilize.

Certain examples streamline the application of these complex operations by combining choosing a series, choosing where to apply the series, and choosing an operation to be applied to the series into one action that involves a minimal amount of mouse movement. By streamlining the workflow for applying complex operations into an action normally associated with the manual hanging of an exam, one of the more complicated parts of an exam setup is eliminated. Radiology departments (especially in the United States) are paid per exam read. Additionally, the amount paid may increase if advanced operations are performed by the radiologist during the exam.

Certain examples help streamline an image series selection process by providing a preview representation that shows a user what they will see without requiring a load of the full image. The preview representation can be provided within the user's current workflow, for example. This allows the user to focus more of his or her time on value added work (e.g., reading the images). Additionally, by providing access to non-image data in the same workflow, the user is able to load and read this information much faster than in prior approaches.

Certain examples provide systems and methods that help make the process of selecting and displaying data from any other source than the primary exam easier and more intuitive than the current state of the art. The navigator tool uses built in intelligence to execute manual steps, while still keeping the application flexible. The navigator helps improve efficiency by allowing the user to perform an operation in fewer steps, while reducing redundancy in loading of undesired exams and in tedious comparison and series navigation through its previewing capabilities.

Certain examples facilitate searching for related data by providing pictorial representations of a comparison series and/or non-image data via the navigator. The navigator to the comparison and non-image data search reduces training time for users, and allows those users who are not able to attend training to utilize the efficiencies discussed above.

The navigator can be used to supplement display and/or hanging protocol(s) by providing more flexibility to the user after the exam is displayed using the protocol.

Certain examples relate to reading and interpretation of diagnostic imaging studies, stored in their digital representation and searched, retrieved, and read using a PACS and/or other clinical system. Certain examples provide ease of image layout on a display, as well as ease of propagating changes to derivative and related images also being displayed. Certain examples reduce an amount of mouse movement for image arrangement and display and simplify a reading workflow via an overlay grid.

Certain examples provide an architecture and framework for a variety of clinical applications. The framework can include front-end components including but not limited to a Graphical User Interface (GUI) and can be a thin client and/or thick client system to varying degree, which some or all applications and processing running on a client workstation, on a server, and/or running partially on a client workstation and partially on a server, for example.

FIG. 1 depicts an example user interface 100 for reviewing images. The interface 100 includes a navigator 110 displayed with respect to a plurality of images 120-125. The navigator 110 can remain displayed along with images 120-125 and/or non-image data and/or can be hidden until triggered by a user and/or event. For example, a mouse and/or keyboard action, such as a double right click of a mouse, can be used to retrieve the navigator 110 in the interface 100. The example navigator 110 can include a representation of all images in a particular exam, for example.

The navigator 110 shown in the example of FIG. 1 illustrates a display layout with block(s) filled in showing which series are currently displayed. One or more comparisons for a particular exam can be loaded into the navigator 110. The navigator 110 reflects the current layout of images 120-125 in a miniature layout 130 and enables a user to change that layout through dragging and dropping and/or other placement of image and/or non-image content. The navigator 110 can show a thumbnail and/or other listing 140 of all available images for one or more exam series so that a user can select one or more image thumbnails 140 and place them in the layout via the mini-layout 130 and/or by directly placing them on the display layout in a position 120-125, for example.

In certain examples, a mouse and/or keyboard action with respect to the navigator 110, such as a click or double click of a mouse, can provide a popup of all comparisons for a particular series labeled by date, such as via the thumbnail listing 140. The user can drag one or more comparisons to the navigator mini-layout 130 and/or to a monitor layout for display, for example.

In certain examples, a user can interact with the navigator 110 (e.g., by using a mouse wheel and/or hot keys) to change a monitor configuration dynamically while in the navigator 110. For example, a user can access the navigator 110 and select a mini-layout view 112. The user can then select an operation 150 to perform (e.g., coronal, sagittal, volume, etc.). The selected operation can then be applied to one or more images in the layout (e.g., take one operation from one image and drag it on to another image to do image subtraction, etc.). A user can interact with the navigator 110 to get specialized views (e.g., sagittal, coronal, and 3D all at once), for example. The navigator 110 can be used to provide a thick slab scroll so that a user can navigate through thick slabs quickly and then return to a more detailed slice on the right. The navigator 110 can provide mammography views as well, for example.

As shown in the example of FIG. 1, a user can pin or affix 114 a location of the navigator 110 in the display layout so that the navigator 110 will open up in the same spot upon next login. Additionally, a user can specify a horizontal or vertical orientation 116 via the navigator 110.

In certain examples, the navigator 110 is aware of information displayed on the screen and is able to examine pixels of images to identify a blackest space on the screen to position the navigator 110 (e.g., "intelligent" positioning). In certain examples, this positioning can be overridden by user manual placement and/or pinning.

Using the example navigator 110, the mini-layout 130 can provide positioning and other information for one or more images being displayed on a display layout. Selected image(s) can be highlighted 160-162 in the mini-layout 130. Identification information 170 can be provided for one or more of the highlighted images 160-162, for example. One or more images can be compared and/or operation(s) can be performed on one or more images via the mini-layout 130, for example. In certain examples, the navigator 110 and mini-layout 130 can be used to assemble a preview of images in a series that can be loaded on the display(s).

In certain examples, images can be displayed automatically according to image type. For example, magnetic resonance MR) images can automatically be displayed in stack mode, and computed tomography (CT) images can automatically be displayed one-up, two-up, etc., in a sheet. User preference and/or intervention can override and/or adjust these automated settings, for example. In certain examples, non-image data and/or application can be positioned as another thumbnail in a preview or mini-layout 130 for placement on a display. For example, a scanned document or report can be provided as a thumbnail in a navigator preview so that a user can hang it just like an image series. In certain examples, an actual report and/or link to a report and/or external application can be provided via the navigator 110 as part of the layout on the display.

The navigator 110 provides flexibility over a hanging protocol and can be used in conjunction with one or more hanging and/or display protocols, for example. If a user does not have what he or she wants or needs in the hanging protocol, the user can access the function using the navigator, and/or the user can use the navigator without a hanging protocol, for example. In certain examples, the navigator 110 can be accessed from a worklist, patient jacket, etc., to see thumbnails and hang them. In certain examples, one navigator can interact with and affect multiple displays. In certain examples, one navigator is provided per configured monitor, for example.

Figure 2:
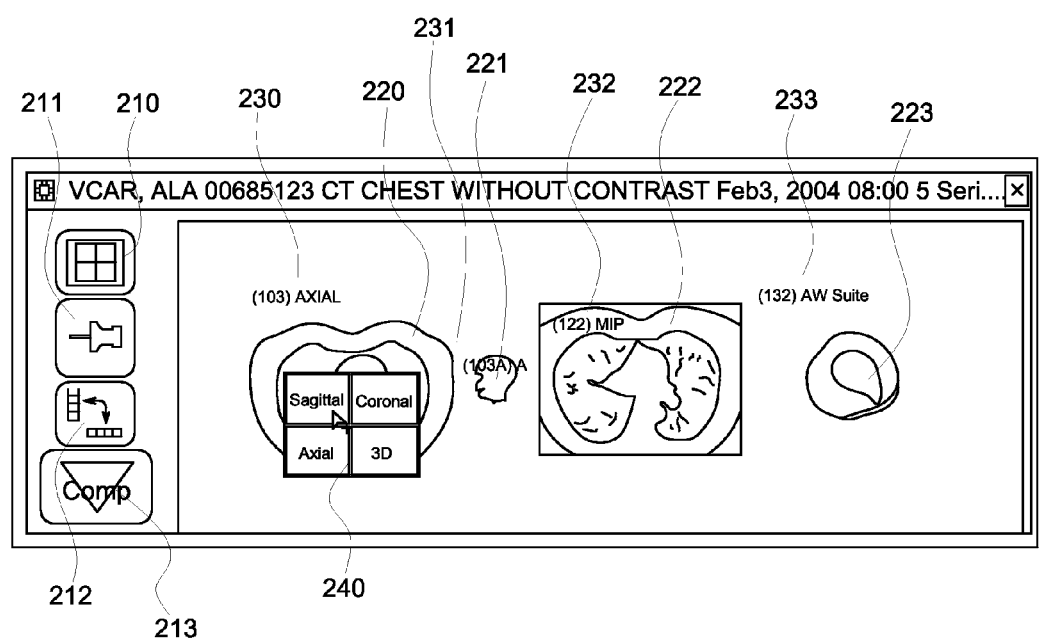
FIG. 2 illustrates an example navigator showing a plurality of images available for preview, display, and operation.

FIG. 2 illustrates an example navigator 200 showing a plurality of images 220-223 available for preview, display, and operation. The example navigator 200 includes a mini-layout 210 to enable a user to preview, position, and apply one or more operation(s) to images in a layout on one or more displays. The example navigator 200 includes a pin 211 to enable a user to position the navigator 200 at a certain position on a display such that the navigator 200 position is remembered for subsequent use. The example navigator 200 includes an orientation selector 212 to enable horizontal or vertical orientation of images and/or other data. The example navigator 200 includes a comparison 213 feature allowing two or more images and/or image series to be compared in preview and/or full layout mode, for example.

As shown in the example of FIG. 2, the navigator 200 provides a thumbnail or image representation preview of one or more available images 220-223 in one or more available series. The images 220-223 can include labels 230-233 identifying a type and/or source of the image, for example. Using the navigator 200, one or more image operations 240 (e.g., sagittal, coronal, axial, 3D, etc.) can be applied to one or more images 220-223.

As demonstrated, for example, in FIG. 2, a user can mouse click to provide an operations menu 240 with respect to an image 220 in the navigator 200. The user can select one or more operations from the operations menu 240 and apply the operation(s) to the selected image 220. In certain examples, operation(s) can be applied to one or more images 220-223 by selecting the one or more images 220-223 and/or be dragging an operation from one image to another, for example.

Figure 3:
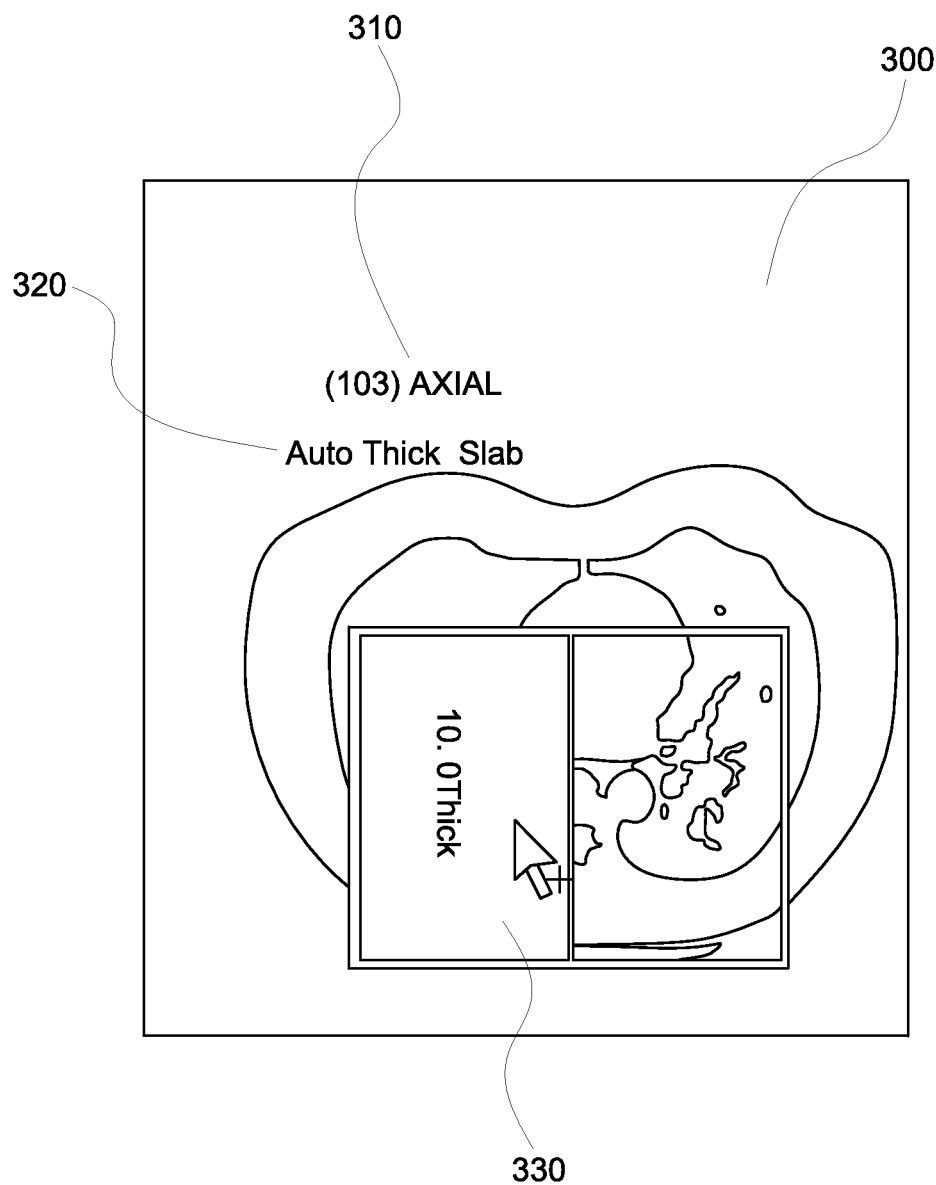
FIG. 3 provides an example image thumbnail representation from a navigator mini-layout.

FIG. 3 depicts an example image thumbnail 300 representation from a navigator mini-layout. As shown in the example of FIG. 3, the thumbnail 300 can include an image label 310 and an indication of an operation 320 (e.g., auto thick slab) applied to display the image in a monitor layout for a user. Using the navigator, a user can adjust and/or otherwise specify a parameter 330 for the operation (e.g., specifying a slab thickness for a thick slab review, as shown in FIG. 3).

Figure 4:
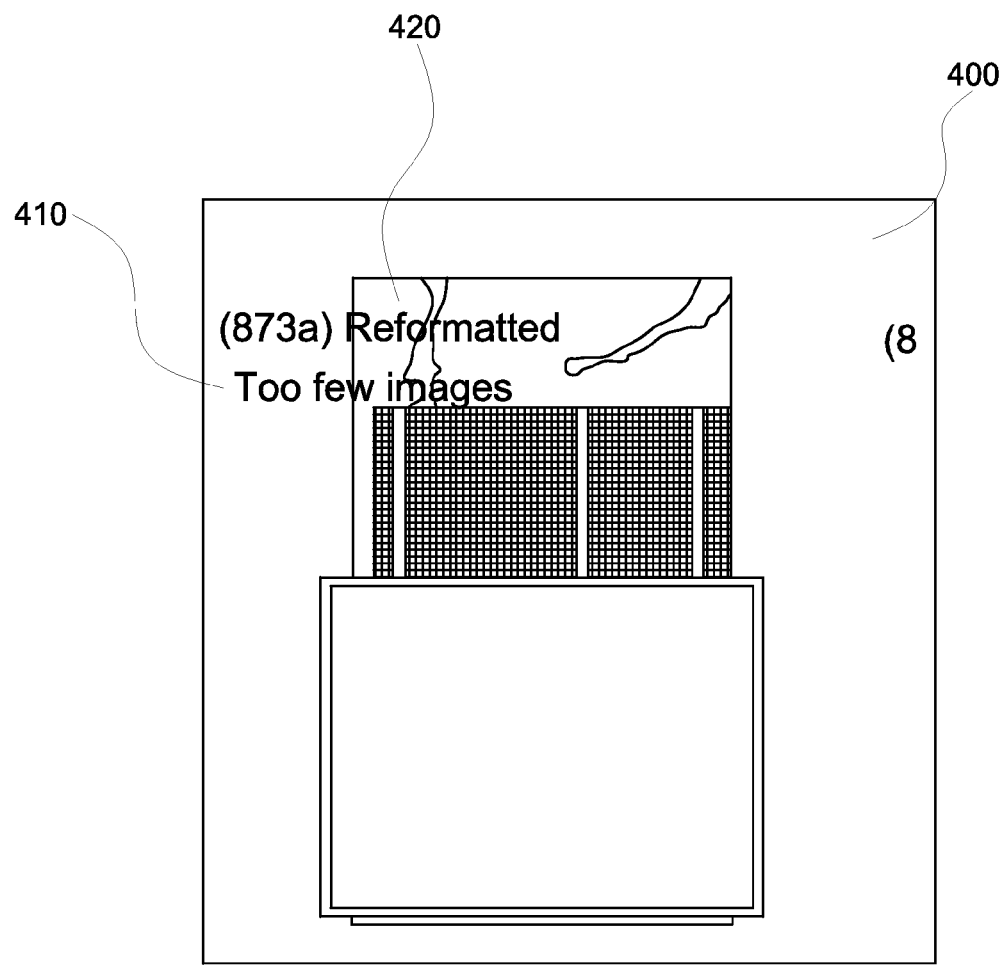
FIG. 4 depicts an example error message generated by a navigator in response to a user operation selection.

In certain examples, a navigator informs a user of an error, incompatibility, or alert/warning based on one or more operations applied to a layout. For example, FIG. 4 depicts an error message 410 indicating that there are too few images that is provided a user with respect to an image thumbnail 400 when a reformatting operation 420 is attempted to be applied to the single image.

Figure 5:
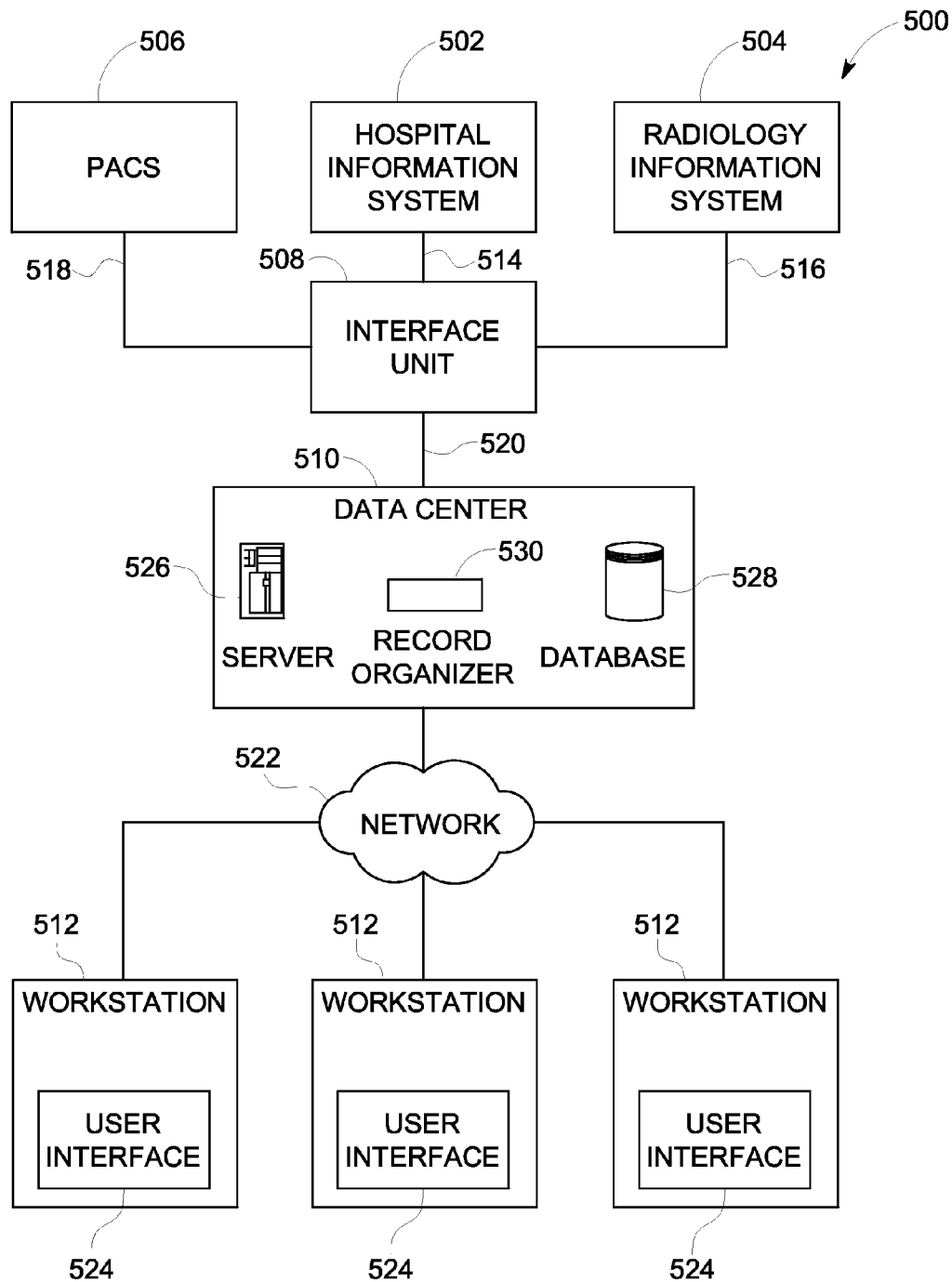
FIG. 5 illustrates a block diagram of an example clinical information system.

FIG. 5 shows a block diagram of an example clinical information system 500 capable of implementing the example methods and systems described herein. The example clinical information system 500 includes a hospital information system (HIS) 502, a radiology information system (RIS) 504, a picture archiving and communication system (PACS) 506, an interface unit 508, a data center 510, and a plurality of workstations 512. In the illustrated example, the HIS 502, the RIS 504, and the PACS 506 are housed in a healthcare facility and locally archived. However, in other implementations, the HIS 502, the RIS 504, and/or the PACS 506 can be housed one or more other suitable locations. In certain implementations, one or more of the PACS 506, RIS 504, HIS 502, etc., can be implemented remotely via a thin client and/or downloadable software solution. Furthermore, one or more components of the clinical information system 500 can be combined and/or implemented together. For example, the RIS 504 and/or the PACS 506 can be integrated with the HIS 502; the PACS 506 can be integrated with the RIS 504; and/or the three example information systems 502, 504, and/or 506 can be integrated together. In other example implementations, the clinical information system 500 includes a subset of the illustrated information systems 502, 504, and/or 506. For example, the clinical information system 500 can include only one or two of the HIS 502, the RIS 504, and/or the PACS 506. Information (e.g., scheduling, test results, observations, diagnosis, etc.) can be entered into the HIS 502, the RIS 504, and/or the PACS 506 by healthcare practitioners (e.g., radiologists, physicians, and/or technicians) before and/or after patient examination.

The HIS 502 stores medical information such as clinical reports, patient information, and/or administrative information received from, for example, personnel at a hospital, clinic, and/or a physician's office. The RIS 504 stores information such as, for example, radiology reports, messages, warnings, alerts, patient scheduling information, patient demographic data, patient tracking information, and/or physician and patient status monitors. Additionally, the RIS 504 enables exam order entry (e.g., ordering an x-ray of a patient) and image and film tracking (e.g., tracking identities of one or more people that have checked out a film). In some examples, information in the RIS 504 is formatted according to the HL-7 (Health Level Seven) clinical communication protocol.

The PACS 506 stores medical images (e.g., x-rays, scans, three-dimensional renderings, etc.) as, for example, digital images in a database or registry. In some examples, the medical images are stored in the PACS 506 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 506 for storage. In some examples, the PACS 506 can also include a display device and/or viewing workstation to enable a healthcare practitioner to communicate with the PACS 506.

The interface unit 508 includes a hospital information system interface connection 514, a radiology information system interface connection 516, a PACS interface connection 518, and a data center interface connection 520. The interface unit 508 facilities communication among the HIS 502, the RIS 504, the PACS 506, and/or the data center 510. The interface connections 514, 516, 518, and 520 can be implemented by, for example, a Wide Area Network ("WAN") such as a private network or the Internet. Accordingly, the interface unit 508 includes one or more communication components such as, for example, an Ethernet device, an asynchronous transfer mode ("ATM") device, an 802.11 device, a DSL modem, a cable modem, a cellular modem, etc. In turn, the data center 510 communicates with the plurality of workstations 512, via a network 522, implemented at a plurality of locations (e.g., a hospital, clinic, doctor's office, other medical office, or terminal, etc.). The network 522 is implemented by, for example, the Internet, an intranet, a private network, a wired or wireless Local Area Network, and/or a wired or wireless Wide Area Network. In some examples, the interface unit 508 also includes a broker (e.g., a Mitra Imaging's PACS Broker) to allow medical information and medical images to be transmitted together and stored together.

In operation, the interface unit 508 receives images, medical reports, administrative information, and/or other clinical information from the information systems 502, 504, 506 via the interface connections 514, 516, 518. If necessary (e.g., when different formats of the received information are incompatible), the interface unit 508 translates or reformats (e.g., into Structured Query Language ("SQL") or standard text) the medical information, such as medical reports, to be properly stored at the data center 510. The reformatted medical information can be transmitted using a transmission protocol to enable different medical information to share common identification elements, such as a patient name or social security number. Next, the interface unit 508 transmits the medical information to the data center 510 via the data center interface connection 520. Finally, medical information is stored in the data center 510 in, for example, the DICOM format, which enables medical images and corresponding medical information to be transmitted and stored together.

The medical information is later viewable and easily retrievable at one or more of the workstations 512 (e.g., by their common identification element, such as a patient name or record number). The workstations 512 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 512 receive commands and/or other input from a user via, for example, a keyboard, mouse, track ball, microphone, etc. As shown in FIG. 5, the workstations 512 are connected to the network 522 and, thus, can communicate with each other, the data center 510, and/or any other device coupled to the network 522. The workstations 512 are capable of implementing a user interface 524 to enable a healthcare practitioner to interact with the clinical information system 500. For example, in response to a request from a physician, the user interface 524 presents a patient medical history. Additionally, the user interface 524 includes one or more options related to the example methods and apparatus described herein to organize such a medical history using classification and severity parameters.

The example data center 510 of FIG. 5 is an archive to store information such as, for example, images, data, medical reports, and/or, more generally, patient medical records. In addition, the data center 510 can also serve as a central conduit to information located at other sources such as, for example, local archives, hospital information systems/radiology information systems (e.g., the HIS 502 and/or the RIS 504), or medical imaging/storage systems (e.g., the PACS 506 and/or connected imaging modalities). That is, the data center 510 can store links or indicators (e.g., identification numbers, patient names, or record numbers) to information. In the illustrated example, the data center 510 is managed by an application server provider ("ASP") and is located in a centralized location that can be accessed by a plurality of systems and facilities (e.g., hospitals, clinics, doctor's offices, other medical offices, and/or terminals). In some examples, the data center 510 can be spatially distant from the HIS 502, the RIS 504, and/or the PACS 506 (e.g., at General Electric® headquarters).

The example data center 510 of FIG. 5 includes a server 526, a database 528, and a record organizer 530. The server 526 receives, processes, and conveys information to and from the components of the clinical information system 500. The database 528 stores the medical information described herein and provides access thereto. The example record organizer 530 of FIG. 5 manages patient medical histories, for example. The record organizer 530 can also assist in procedure scheduling, for example.

Images and related data are displayed at a client workstation for radiologist and/or other clinician review. When a user has many images for review and not enough real estate for display of the images on a monitor, the user must drag images from the navigator to an area on the monitor for large scale review. Such a manual approach involves much mouse movement and user fatigue.

In certain examples, a review workstation display can be configured and divided into a plurality of segments or quadrants to display multiple images and/or other data. Images and/or other data can be placed in the segments of the display automatically based on certain parameters and/or based on user preference, for example. Software running on the workstation can keep track of how many segments have been created on the display and what content is displayed in which segment (if any). Software running on the workstation can interact in thick and/or thin client operation to retrieve images and/or other data locally and/or remotely for display in one or more segments, for example. Images and/or other data can be from the same and/or multiple modalities, for example.

Hanging protocols can be used to define an arrangement of images and/or other information on a display. A workflow may involve an overview set of images and more focused sets of images. The workflow may require stepping through various configurations of images. A typical workflow can be an array or sequence of hangings, for example. This sequence of hangings can be saved as one piece, which may not be convenient because each step can be part of multiple sequences. Therefore, certain embodiments allow creation of a hanging protocol and saving of all or part of the hanging protocol as a separate object. The hanging protocol can be saved on multiple levels (e.g., common, group, private) depending upon a level at which sharing of tools and information with other users is desired. Additionally, certain embodiments provide a layout editor that allows a user to select which hanging protocol(s) from a library the user wants to apply to a particular layout for a sequence. An alignment tool can be used to create the hanging protocols and separate the workspace into a set of rectangles or set of nested rectangles. A user can populate the workspace with a series by dragging thumbnails into the rectangles.

In certain examples, a user can set matching criteria directly when dragging and dropping series images into rectangles, rather than manually selecting the matching criteria (e.g., sequential, by description, by orientation, by modality, etc), and the matching criteria is displayed in conjunction with the image. Placeholders can be allocated for series, as well as any presentation object and for derived data. For example, a user and/or application can reserve a place for a navigator, key images, fused images (derived from original series), etc. When deriving an image, a user and/or application can specify what the sources should be and can specify what is important in the series (e.g., description, contrast flag, attenuation corrected, etc.). Placeholder behavior properties can also be specified (e.g., activated upon opening, run cine, specify frame rate, continuous/non-continuous in a certain direction, etc.). A mouse mode can be specified in the hanging protocol (scrolling, triangulation, magnify, etc.). Comparison hangings can be created. Comparison hangings can be created for multiple modalities. For example, a hanging protocol can be created for comparison between CT and MR images, and this hanging protocol will be applied automatically when a certain combination of studies is selected for display.

For example, twelve images are included in a study, but a layout has room for eight images. A layout can be created including a placeholder for an overview wherein an image not previously displayed is a candidate to display in that placeholder. Multiple overview placeholders can be specified, for example.

Additionally, an indicator can be provided to indicate whether a viewer has seen the images. For example, an image thumbnail can include a red rectangle indicating that the image has not been reviewed. A yellow triangle can indicate that the image has been partially been reviewed, for example. A green circle can indicate that the image has been reviewed, for example. Color and shape coding (e.g., for black and white monitors) can be used on the series and represented on both a thumbnail and a full image, for example.

Figure 6:
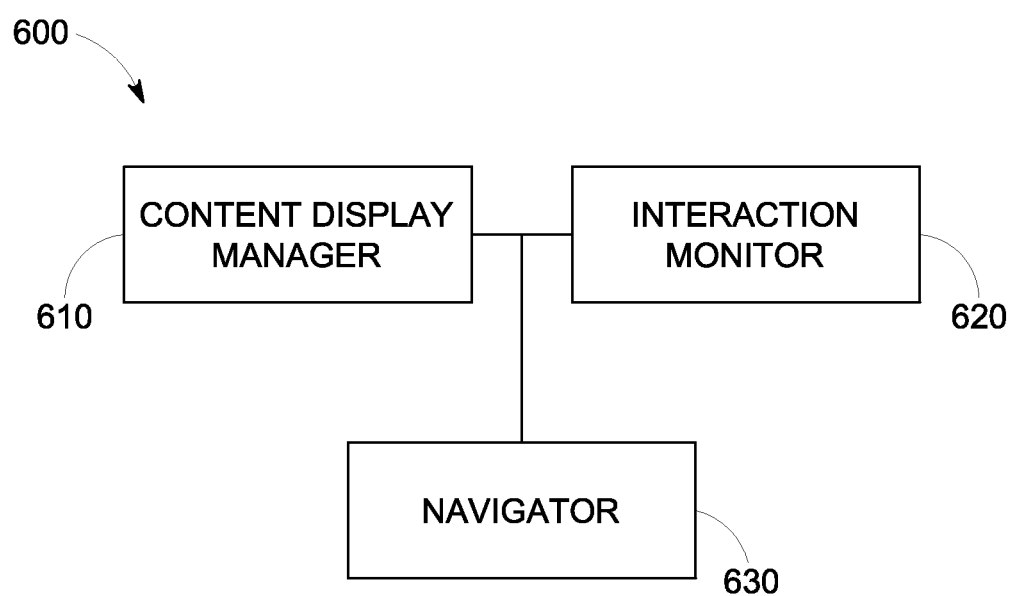
FIG. 6 illustrates an example navigator system enabling a user to more easily navigate and position images and/or other data on a display and apply operations to the image(s) and/or other data.

FIG. 6 illustrates an example navigator system 600 enabling a user to more easily navigate and position images and/or other data on a display and apply operations to the image(s) and/or other data. The system 600 includes a content display manager 610, an interaction monitor 620, and a navigator 630. The content display manager 610 controls images and/or other information displayed on a workstation for user review. The interaction monitor 620 monitors user interaction with the workstation and with the content displayed. Upon entering a certain mode, for example, the interaction monitor 620 monitors cursor movement, mouse clicks, and cursor location on the workstation display. Such monitored action can trigger the appearance and use of the navigator 630. The navigator 630 includes one or more sections corresponding to a division of the display. The navigator 630 indicates which sections are occupied, unoccupied, reserved, and/or related (e.g., derivative, simulated, etc.), for example. An action in the navigator 630 translates into an action on the display and vice versa, for example.

For example, if a user initiates dragging an image to a location on the display, the interaction monitor 620 triggers the navigator 630 to appear. The user can then drop the image into a section of the navigator 630. As another example, a certain key press or movement of the cursor displays the navigator 630 for positioning. The navigator 630 can be overlaid on the display and include a certain degree of transparency to allow underlying images and/or other data on the display to continue to be seen by the user. A user can also drag and drop an image into an open section of the display without using the navigator 630, for example.

In certain examples, the content display manager 610, interaction monitor 620, and navigator 630 can work in conjunction with a hanging/display protocol and/or other user preference and/or system parameter, for example.

The content display manager 610, interaction monitor 620, and navigator 630 can be implemented in software, hardware, firmware, and/or a combination of these elements. The content display manager 610, interaction monitor 620, and navigator 630 can be implemented separately and/or combined in various forms. The content display manager 610, interaction monitor 620, and navigator 630 can be implemented as a set of instructions/routines forming machine executable code stored on a machine accessible medium for execution by a computing/processing device, for example.

Figure 7:
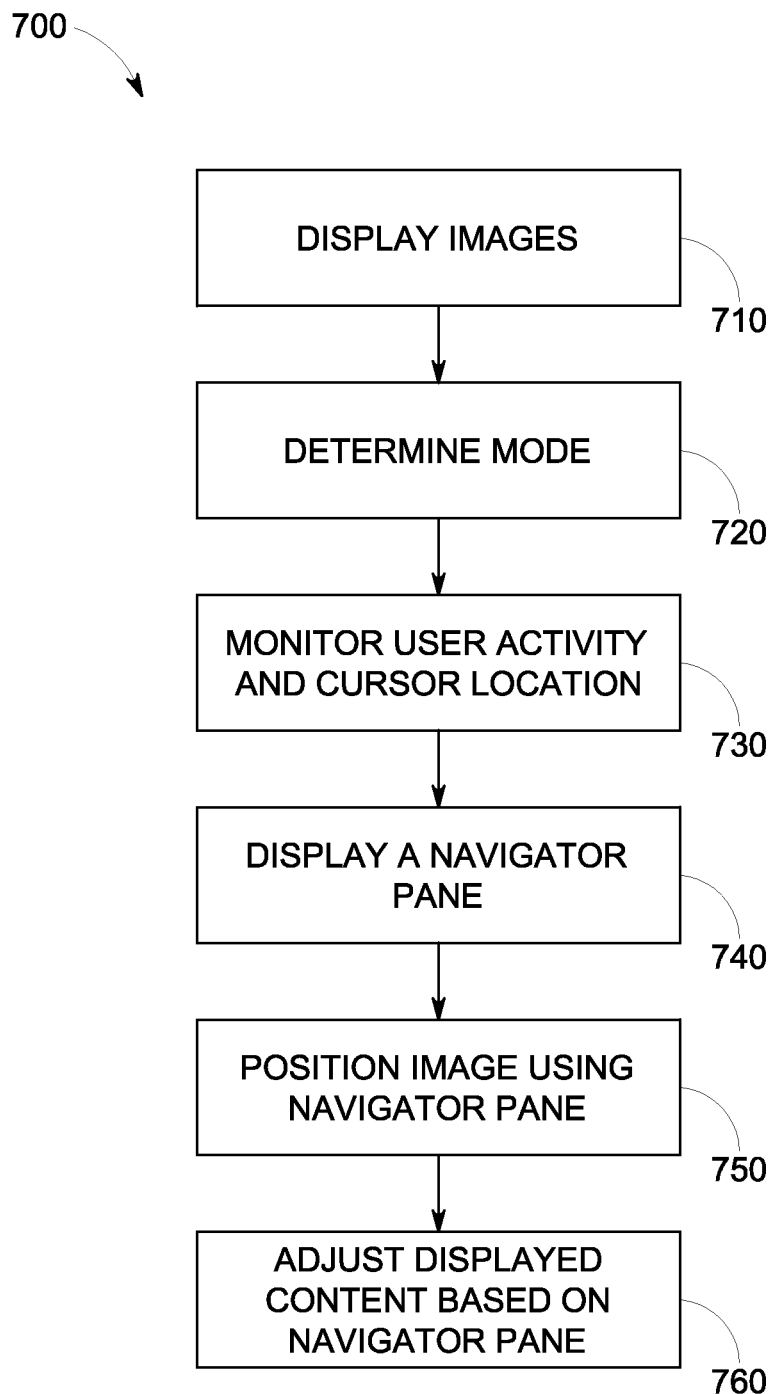
FIG. 7 illustrates a flow diagram for an example method for positioning images and/or other data on a display using a navigator.

FIG. 7 depicts a flow diagram representative of example machine readable instructions that can be executed to implement the example systems shown in FIGS. 1-6 and/or portions of one or more of those systems. The example process(es) of FIG. 7 can be performed using a processor, a controller and/or any other suitable processing device. For example, the example process(es) of FIG. 7 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example process(es) of FIG. 7 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example process(es) of FIG. 7 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example process(es) of FIG. 7 can be implemented manually or as any combination(s) of any of the foregoing techniques, for example, any combination of firmware, software, discrete logic and/or hardware. Further, although the example process(es) of FIG. 7 are described with reference to the flow diagram of FIG. 7, other methods of implementing the process(es) of FIG. 7 can be employed. For example, the order of execution of the blocks can be changed, and/or some of the blocks described can be changed, eliminated, sub-divided, or combined. Additionally, any or all of the example process(es) of FIG. 7 can be performed sequentially and/or in parallel by, for example, separate processing threads, processors, devices, discrete logic, circuits, etc.

FIG. 7 illustrates a flow diagram for an example method 700 for positioning images and/or other data on a display using a navigator. At block 710, images and/or other information are displayed. For example, a series of computed tomography images are displayed in sections of a PACS workstation display.

At block 720, entry into a certain mode, such as a navigation or layout mode, is determined. At block 730, upon entering the certain mode, such as a navigation or layout mode, cursor movement, user activity (e.g., mouse clicks), and cursor location on the workstation display are monitored.

At block 740, a navigator pane is displayed. For example, user/cursor action monitored above can trigger the appearance and use of the navigator pane. The navigator pane can include one or more sections corresponding to one or more sections dividing a display. The navigator pane indicates which sections of the display are occupied, unoccupied, reserved, and/or related (e.g., derivative, simulated, etc.), for example. The navigator pane may be a semi-transparent overlay on at least a portion of the display, for example. The navigator pane can appear in close proximity to an image being moved, for example. An action in the navigator pane translates into an action on the display and vice versa, for example.

For example, if a user initiates dragging an image to a location on the display, the navigator pane can be triggered to appear. As another example, a certain key press or movement of the cursor can display the navigator pane for positioning.

At 750, an image and/or other data is positioned in a section of the navigator pane. For example, a user can select an image to trigger the navigator pane to appear and can then select a section of the navigator pane to indicate a desired position for the image on the display.

At 760, displayed content is adjusted based on the content of the navigator pane. For example, if a user moved an image into a section of the navigator pane, the image is displayed in the corresponding section of the workstation display. Additionally, changes in displayed content and layout can be propagated to derivative and related images also being displayed. In certain examples, one or more operations can be applied to one or more images being displayed by selecting an image and/or multiple images in a navigator layout. In certain examples, operation(s) can be propagated from one image to another by dragging an operation from one image in a navigator mini-layout to another image in the navigator mini-layout and/or by dragging and dropping one image on top of another image in the navigator mini-layout. Operation(s) and change(s) facilitated by the navigator are applied and reflected in the actual images being displayed on a single and/or multi-monitor layout, for example.

One or more of the blocks of the method 700 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these blocks and/or perform the blocks in a different order than the order listed. For example, some steps may not be performed in certain examples. As a further example, certain steps may be performed in a different temporal order, including simultaneously, than listed above.

Figure 8:
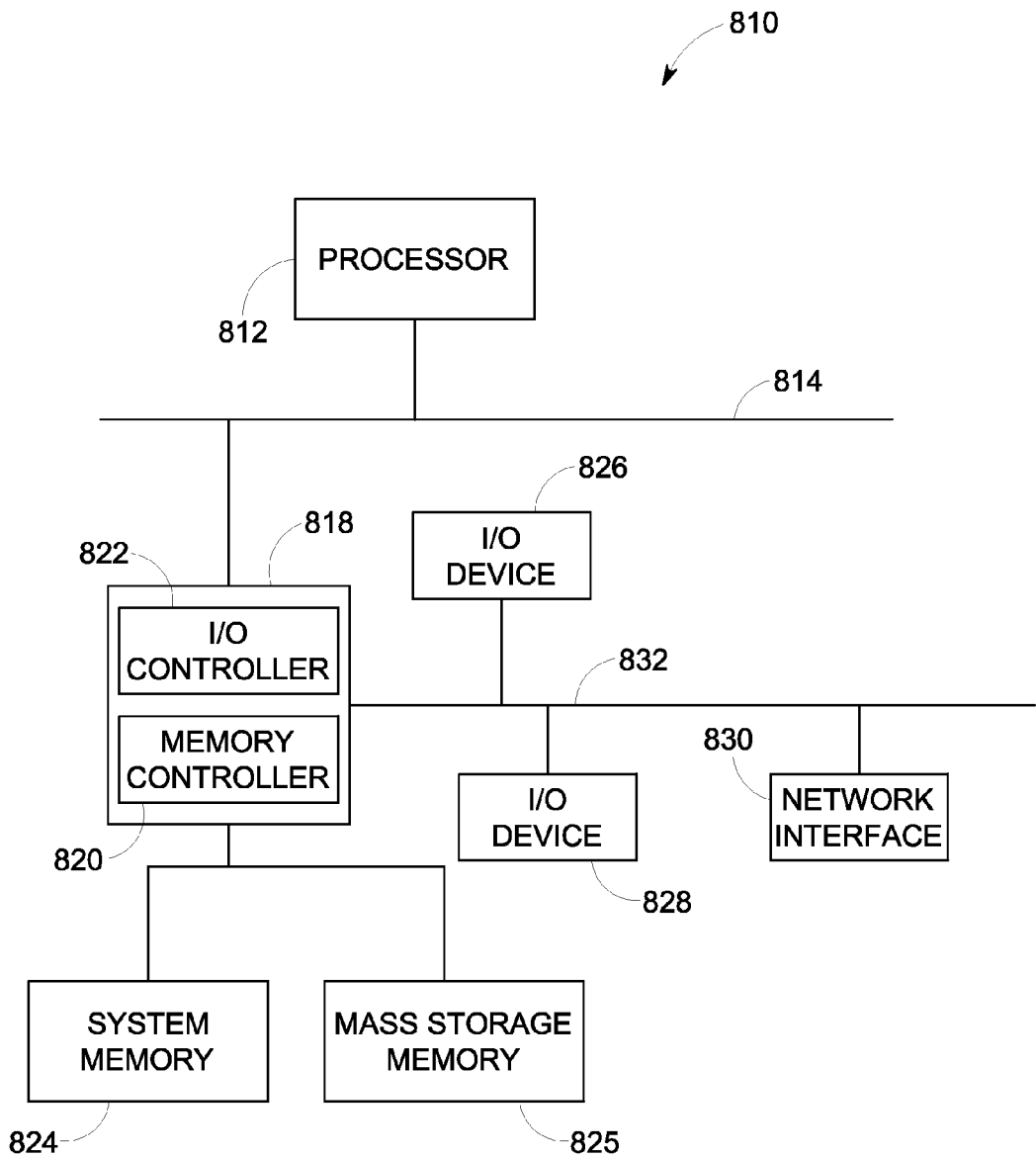
FIG. 8 shows a block diagram of an example processor system that may be used to implement systems and methods described herein.

FIG. 8 is a block diagram of an example processor system 810 that can be used to implement systems and methods described herein. As shown in FIG. 8, the processor system 810 includes a processor 812 that is coupled to an interconnection bus 814. The processor 812 can be any suitable processor, processing unit, or microprocessor, for example. Although not shown in FIG. 8, the system 810 can be a multi-processor system and, thus, can include one or more additional processors that are identical or similar to the processor 812 and that are communicatively coupled to the interconnection bus 814.

The processor 812 of FIG. 8 is coupled to a chipset 818, which includes a memory controller 820 and an input/output ("I/O") controller 822. As is well known, a chipset typically provides I/O and memory management functions as well as a plurality of general purpose and/or special purpose registers, timers, etc. that are accessible or used by one or more processors coupled to the chipset 818. The memory controller 820 performs functions that enable the processor 812 (or processors if there are multiple processors) to access a system memory 824 and a mass storage memory 825.

The system memory 824 can include any desired type of volatile and/or non-volatile memory such as, for example, static random access memory (SRAM), dynamic random access memory (DRAM), flash memory, read-only memory (ROM), etc. The mass storage memory 825 can include any desired type of mass storage device including hard disk drives, optical drives, tape storage devices, etc.

The I/O controller 822 performs functions that enable the processor 812 to communicate with peripheral input/output ("I/O") devices 826 and 828 and a network interface 830 via an I/O bus 832. The I/O devices 826 and 828 can be any desired type of I/O device such as, for example, a keyboard, a video display or monitor, a mouse, etc. The network interface 830 can be, for example, an Ethernet device, an asynchronous transfer mode ("ATM") device, an 802.11 device, a DSL modem, a cable modem, a cellular modem, etc. that enables the processor system 810 to communicate with another processor system.

While the memory controller 820 and the I/O controller 822 are depicted in FIG. 8 as separate blocks within the chipset 818, the functions performed by these blocks can be integrated within a single semiconductor circuit or may be implemented using two or more separate integrated circuits.

Thus, certain examples provide for improved reading and interpretation of diagnostic imaging studies via a reviewing workstation, such as a PACS workstation. Certain examples provide a technical effect of user control over content layout on a display and improved ease of image layout, as well as ease of propagating changes to derivative and/or other related content also being displayed. Certain examples reduce an amount of mouse movement for image arrangement and display and simplify a reading workflow via an overlay grid.

Certain examples contemplate methods, systems and computer program products on any machine-readable media to implement functionality described above. Certain examples can be implemented using an existing computer processor, or by a special purpose computer processor incorporated for this or another purpose or by a hardwired and/or firmware system, for example.

One or more of the components of the systems and/or steps of the methods described above can be implemented alone or in combination in hardware, firmware, and/or as a set of instructions in software, for example. Certain examples can be provided as a set of instructions residing on a computer-readable medium, such as a memory, hard disk, DVD, or CD, for execution on a general purpose computer or other processing device. Certain examples of the present invention can omit one or more of the method steps and/or perform the steps in a different order than the order listed. For example, some steps cannot be performed in certain examples of the present invention. As a further example, certain steps can be performed in a different temporal order, including simultaneously, than listed above.

Certain examples include computer-readable media for carrying or having computer-executable instructions or data structures stored thereon. Such computer-readable media can be any available media that can be accessed by a general purpose or special purpose computer or other machine with a processor. By way of example, such computer-readable media can comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory can include read only memory (ROM) and random access memory (RAM). The computer can also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for image review and series operations using a navigator for a display, said method comprising:
    displaying a layout of images shown via a user interface on a display;
    displaying a navigator interface in conjunction with the layout, the navigator interface displayed based on user action with respect to content displayed on the display and comprising an overlay on at least a portion of the layout of images and providing, in response to a selection via the navigator interface, a miniature layout representation corresponding to the layout of images on the display;
    accepting user selection of an image series via the navigator's miniature layout;
    providing one or more series level operations for application to the selected image series via the miniature layout, the one or more series level operations configured to modify the display of one or more images in the selected image series;
    facilitating selection of a series level operation to apply to the selected image series via the miniature layout;
    providing, based on the selection of the series level operation, (i) a preview of application of the selected series level operation to the selected image series via the miniature layout before the selected series level operation is applied to the selected image series and (ii) a visual indication of operation status such that a) when the selected series level operation is not precluded, the visual indication shows the selected series level operation to be applied to the selected image series and b) when the selected series level operation is precluded, the visual indication shows an error message indicating a condition that precludes application of the selected series level operation to the selected image series;
    if the selected series level operation is not precluded, applying the selected series level operation to the selected image series via the miniature layout based on user input; and
    updating display of the layout of images on the display based on the selected series level operation.

2. The method of claim 1, further comprising alerting the user regarding the condition affecting the selected series level operation.

3. The method of claim 1, wherein the one or more series level operations includes three dimensional reformatting of the selected image series.

4. The method of claim 1, wherein the one or more series level operations includes applying and examining interactions between two selected image series.

5. The method of claim 1, wherein the one or more series level operations includes providing a comparison preview between at least one of 1) two image series and 2) an image in the selected image series and another comparison image.

6. The method of claim 1, wherein the one or more series level operations includes applying the selected series level operation to all images in the selected image series.

7. The method of claim 1, wherein the one or more series level operations includes applying a predefined layout to the selected image series for a special function view.

8. The method of claim 1, wherein the miniature layout is a multiple image preview sheet for user review and selection.

9. The method of claim 1, wherein the navigator's miniature layout enables user placement of image and non-image data in the layout on the display.

10. An image layout and display navigator system, said system comprising:
- a processor configured to implement:
  - a content display manager to control content displayed for a user on a display, the content organized on the display according to a layout including multiple regions displayed via a user interface; and
  - a navigator to include a miniature layout representation corresponding to the layout of content on the display, the miniature layout to appear in response to a selection via the navigator and the navigator to appear as an overlay on at least a portion of the displayed layout of images based on user action with respect to content displayed on the display and to allow a user to select an image series via the miniature layout and to select one or more series level operations for application to the selected image series via the miniature layout, the one or more series level operations configured to modify the display of the one or more images in the selected image series, the navigator to provide, based on the selection of the series level operation, (i) a preview of application of the selected series level operation to the selected image series via the miniature layout before the selected series level operation is applied to the selected image series and (ii) a visual indication of operation status such that a) when the selected series level operation is not precluded, the visual indication shows the selected series level operation to be applied to the selected image series and b) when the selected series level operation is precluded, the visual indication shows an error message indicating a condition that precludes application of the selected series level operation to the selected image series, wherein if the selected series level operation is not precluded, the navigator is to apply the selected series level operation to the selected image series via the miniature layout based on user input, wherein an action in one of the navigator and the display translates into a corresponding action on the other of the navigator and the display, and wherein the content display manager is to update content displayed on the display to reflect the selected series level operation applied to the selected image series.

11. The system of claim 10, wherein the navigator is to alert the user regarding the condition affecting the selected series level operation.

12. The system of claim 10, wherein the one or more series level operations includes three dimensional reformatting of the selected image series.

13. The system of claim 10, wherein the one or more series level operations includes applying and examining interactions between two selected image series.

14. The system of claim 10, wherein the one or more series level operations includes providing a comparison preview between at least one of 1) two image series and 2) an image in the selected image series and another comparison image.

15. The system of claim 10, wherein the one or more series level operations includes applying the selected series level operation to all images in the selected image series.

16. The system of claim 10, wherein the one or more series level operations includes applying a predefined layout to the selected image series for a special function view.

17. The system of claim 10, wherein the miniature layout is a multiple image preview sheet for user review and selection.

18. The system of claim 10, wherein the navigator's miniature layout enables user placement of image and non-image data in the layout on the display.

19. The system of claim 10, wherein the navigator automatically changes the displayed layout when an image thumbnail is dropped onto a region based on at least one of a modality, procedure, and body part to be displayed.

20. The system of claim 10, further comprising a plurality of linked navigators each corresponding to a display in a multiple monitor configuration, wherein each of the plurality of linked navigators is to control operations on its corresponding display.

21. A non-transitory computer readable medium having a set of instructions for execution on a processing device, the set of instructions implementing image layout and display navigator system, said system comprising:
- a content display manager to control content displayed for a user on a display, the content organized on the display according to a layout including multiple regions displayed via a user interface; and
- a navigator to include a miniature layout representation corresponding to the layout of content on the display, the miniature layout to appear in response to a selection via the navigator and the navigator to appear as an overlay on at least a portion of the displayed layout of images based on user action with respect to content displayed on the display and to allow a user to select an image series via the miniature layout and to select one or more series level operations for application to the selected image series via the miniature layout, the one or more series level operations configured to modify the display of the one or more images in the selected image series, the navigator to provide, based on the selection of the series level operation, (i) a preview of application of the selected series level operation to the selected image series via the miniature layout before the selected series level operation is applied to the selected image series and (ii) a visual indication of operation status such that a) when the selected series level operation is not precluded, the visual indication shows the selected series level operation to be applied to the selected image series and b) when the selected series level operation is precluded, the visual indication shows an error message indicating a condition that precludes application of the selected series level operation to the selected image series, wherein if the selected series level operation is not precluded, the navigator is to apply the selected series level operation to the selected image series via the miniature layout based on user input, wherein an action in one of the navigator and the display translates into a corresponding action on the other of the navigator and the display, and wherein the content display manager is to update content displayed on the display to reflect the selected series level operation applied to the selected image series.

* * * * *

UNITED STATES PATENT AND TRADEMARK OFFICE
CERTIFICATE OF CORRECTION

| | | |
|---|---|---|
| PATENT NO. | : 9,262,444 B2 | |
| APPLICATION NO. | : 12/954282 | |
| DATED | : February 16, 2016 | |
| INVENTOR(S) | : Ryan Wayne Gross and Joseph Carroll | |

It is certified that error appears in the above-identified patent and that said Letters Patent is hereby corrected as shown below:

On the title page item 75 "Inventors: Donna Klem," delete "Donnna Klem" and insert --Donna Klem--.

Signed and Sealed this
Tenth Day of May, 2016

Michelle K. Lee
*Director of the United States Patent and Trademark Office*